United States Patent
Gadgil et al.

(10) Patent No.: US 11,618,768 B2
(45) Date of Patent: Apr. 4, 2023

(54) CONTINUOUS PROCESS FOR REDUCING HETEROGENEITY OF THERAPEUTIC PROTEIN

(71) Applicant: Enzene Biosciences Limited, Pune (IN)

(72) Inventors: Himanshu Gadgil, Pune (IN); Abir Banerjee, Pune (IN); Gopal Dyaga, Pune (IN); Ashvin Pankhania, Pune (IN); Harshita Londhe, Pune (IN); Deepika Rao, Pune (IN)

(73) Assignee: ENZENE BIOSCIENCES LIMITED, Maharashtra (IN)

( * ) Notice: Subject to any disclaimer, the term of this patent is extended or adjusted under 35 U.S.C. 154(b) by 408 days.

(21) Appl. No.: 16/340,822

(22) PCT Filed: Oct. 16, 2017

(86) PCT No.: PCT/IB2017/056395
§ 371 (c)(1),
(2) Date: Apr. 10, 2019

(87) PCT Pub. No.: WO2018/073717
PCT Pub. Date: Apr. 26, 2018

(65) Prior Publication Data
US 2019/0263855 A1    Aug. 29, 2019

(30) Foreign Application Priority Data
Oct. 17, 2016  (IN) .............................. 201621035458

(51) Int. Cl.
*C07K 1/16* (2006.01)
*C07K 1/12* (2006.01)
*C07K 1/22* (2006.01)
*C07K 16/00* (2006.01)

(52) U.S. Cl.
CPC ............ *C07K 1/16* (2013.01); *C07K 1/12* (2013.01); *C07K 1/22* (2013.01); *C07K 16/00* (2013.01)

(58) Field of Classification Search
CPC ... C07K 1/16; C07K 1/12; C07K 1/22; C07K 16/00
See application file for complete search history.

(56) References Cited

U.S. PATENT DOCUMENTS

2013/0280274 A1* 10/2013 Subramanian ....... C12N 5/0018
                                                           424/172.1
2015/0267237 A1*  9/2015 Meier ..................... C12P 21/00
                                                           424/143.1

OTHER PUBLICATIONS

Girard et al. "Large-scale monoclonal antibody purification by continuous chromatography, from process design to scale-up" Journal of Biotechnology 213 (2015) 65-73 (Year: 2015).*
Kim et al. "Effects of carboxypeptidase B treatment and elevated temperature on recombinant monoclonal antibody charge variants in cation-exchange chromatography analysis" Arch. Pharm. Res. 2016, 39, 1472-1481 (Year: 2016).*
Kudryavtseva et al. "Immobilization of trypsin and carboxypeptidase B on modified silicas and their use in converting human recombinant proinsulin into insulin" Pharmaceutical Chemistry Journal, 29(1), 1995, pp. 61-64 (Year: 1995).*
Yasuhara, "Apocarboxypeptdiase B-sepahrose: a specific adsorbent for peptides" Biochemical and Biophysical. Research Communications, 166(1), pp. 330-335, 1990 (Year: 1990).*
Sudi "Preparation, characterization, and application of a novel immobilized carboxypeptidase B" Oct. 22(1), pp. 31-43, 1989 (Year: 1989).*
Chemuru et al. "Improved chemical synthesis of hydrophobic Abeta peptides using addition of C-terminal Lysines later remvoed by carboxypeptidase B", Peptide Science, 102(2), pp. 206-221, 2014 (Year: 2014).*

* cited by examiner

*Primary Examiner* — Daniel E Kolker
*Assistant Examiner* — James L Rogers
(74) *Attorney, Agent, or Firm* — Dority & Manning, P.A.

(57) ABSTRACT

The present disclosure relates to a bio-manufacturing process that enables continuous production of a therapeutic protein with reduced heterogeneity. The bio-manufacturing process disclosed herein utilizes a multi column chromatography system that performs the unit operations of reducing heterogeneity in a therapeutic protein, capturing the therapeutic protein and inactivating viruses, purifying the therapeutic protein, and polishing the purified therapeutic protein. The process disclosed herein can reduce heterogeneity of a therapeutic protein by reducing a proportion of basic isoforms of the therapeutic protein.

13 Claims, 15 Drawing Sheets

CONTINUOUS PROCESS FOR REDUCING HETEROGENEITY OF THERAPEUTIC PROTEIN

TECHNICAL FIELD

The present disclosure relates to technical field of bio-manufacturing of therapeutic proteins. In particular, the present disclosure relates to continuous process for manufacturing therapeutic proteins with reduced heterogeneity.

BACKGROUND

The background description includes information that may be useful in understanding the present invention. It is not an admission that any of the information provided herein is prior art or relevant to the presently claimed invention, or that any publication specifically or implicitly referenced is prior art.

Identification of significance of therapeutic protein has led to new revolution in biopharmaceutical industry. However, production of therapeutic protein commonly observes their charged isoforms which largely interfere in the isolation and purification processes that are required to attain high yields and quality in the product.

Carboxypeptidase enzyme is commonly used for preparation of homogenous form of therapeutic protein such as monoclonal antibody as it catalyses the hydrolysis of the C-terminal peptide bond. Carboxypeptidase B is a carboxypeptidase that preferentially acts upon basic amino acids, such as arginine and lysine.

Various methods have been disclosed in the prior arts to reduce amount of heterogeneity in therapeutic proteins. For example, U.S. Pat. No. 5,126,250 discloses method of reducing the heterogeneity of secreted antibodies from antibody-producing cells by conversion of most heterogeneous antibodies into one substantially homogeneous form before purification.

WO20120147053 discloses method of reducing heterogeneity in antibodies obtained by cell culturing.

U.S. Pat. No. 9,062,337 discloses utilization of peptidylglycine alpha amidating monooxigenase enzyme for truncating C-terminal residue of peptide.

Various prior art documents have also disclosed the immobilization of enzyme for purification and production of therapeutic proteins. Chemuru et al., Biopolymers 2014 March; 102(2): 206-221 discloses removal of lys residue of Aβ peptide using carboxypeptidase B immobilized onto agarose beads.

Kudryavtseva et al., Pharm Chem J (1995) 29: 70 discloses immobilization of trypsin and carboxypeptidase B on modified silicas for conversion of proinsulin into insulin. Yasuhara and Ohashi, Appl Biochem Biotechnol (1994) 44: 151 discloses immobilization of a pocarboxypeptidase B on sepharose for removal of C-terminal residues of peptide.

U.S. Pat. No. 9,657,056 discloses integrated and continuous processes for manufacturing a therapeutic protein drug substance wherein the liquid culture medium from perfusion bioreactor is transferred on MCCS1 for capture on first three columns out of four columns, and eluate from these is loaded and incubated on fourth column for viral inactivation. The eluate of the MCCS1 containing the recombinant therapeutic protein is continuously fed into a second multi-column chromatography system (MCCS2); and purifying and polishing the recombinant therapeutic protein using the MCCS2.

Removal of heterogeneity from C-terminal residue is normally performed in fed batch culture by addition to carboxypeptidase directly to the bioreactor in the culture medium or right after chromatographic step. However, the addition of enzyme requires a lot of optimization steps in terms of incubation time, temperature, pH, etc. Furthermore, the high cost of enzyme leads to enhancement in the overall cost of process.

Continuous bio-processing has recently gained a large amount of interest because of various advantages like steady-state operation, small equipment size, high volumetric productivity, streamlined process flow, low cycle time and reduced capital cost.

Although number of approaches has been disclosed in the prior art for reducing heterogeneity of therapeutic proteins, none describe a continuous process for producing therapeutic proteins with reduced heterogeneity. The prior art also fails to provide a process that enables reduction of heterogeneity in a protein before purification.

The present invention satisfies the existing needs, as well as others, and generally overcomes the deficiencies found in the prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

OBJECTS OF THE INVENTION

It is an object of the present disclosure to provide a bio-manufacturing process that enables continuous production of therapeutic protein with reduced heterogeneity.

It is another object of the present disclosure to provide a continuous process that enables reduction of heterogeneity in a therapeutic protein before purification step.

It is another object of the present disclosure to provide a continuous process for reducing heterogeneity of a therapeutic protein without compromising the overall yield of the therapeutic protein production.

It is yet another object of the present disclosure to provide a highly flexible and economic bio-manufacturing process that can be used to continuously produce therapeutic protein with reduced heterogeneity.

SUMMARY

Aspects of the present disclosure relate to a bio-manufacturing process that enables continuous production of a therapeutic protein with reduced heterogeneity. The bio-manufacturing process disclosed herein utilizes a multi column chromatography system that performs the unit operations of reducing heterogeneity in a therapeutic protein, capturing the therapeutic protein and inactivating viruses, purifying the therapeutic protein, and polishing the purified therapeutic protein.

In an aspect, the present disclosure provides a continuous process for reducing heterogeneity of a therapeutic protein, the process including reducing one or more basic isoforms of the therapeutic protein in a single multi-column chromatography system.

In an embodiment, the multi-column chromatography system can include at least two chromatography columns.

In an embodiment, the multi-column chromatography system can include a column comprising carboxypeptidase B immobilized on sepharose.

In another aspect, the present disclosure provides a continuous process for reducing heterogeneity of a therapeutic protein, the process can include the steps of:
(a) providing a multi-column chromatography system comprising a first column, a second column, a third column and a fourth column;
(b) feeding a cell culture harvest comprising a therapeutic protein into the first column, thereby reducing heterogeneity of the therapeutic protein; wherein the first column comprising carboxypeptidase B immobilized on sepharose,
(c) feeding a flow-through from the first column into the second column, thereby capturing the therapeutic protein in the flow-through of the first column;
(d) feeding an eluate comprising the therapeutic protein from the second column into the third column to purify the therapeutic protein; and
(e) feeding a flow-through comprising the therapeutic protein from the third column into the fourth column to polish the therapeutic protein.

In an embodiment, an eluate comprising a therapeutic protein from the second column can be collected and held in a reservoir at a low pH for viral inactivation. After viral inactivation, the eluate from the second column can be subjected to pH and conductivity adjustments before it is fed into the third column.

In an embodiment, a flow-through comprising a therapeutic protein from the third column can be subjected to pH and conductivity adjustments before the said flow-through is fed into the fourth column.

In an embodiment, the first, second, third and fourth columns of the multi-column chromatography system can be connected in sequential order in series or in parallel.

In an embodiment, the first column reduces heterogeneity of a therapeutic protein by reducing a proportion of basic isoforms of the therapeutic protein.

In an embodiment, the second column can be an affinity chromatography column.

In an embodiment, each of the third column and fourth column can be selected from the group consisting of anion exchange chromatography column, cation exchange chromatography column, hydrophobic interaction chromatography column, and multimodal chromatography column.

In an embodiment, therapeutic proteins that can be prepared by/used in the process of the present disclosure can include, but not limited to, an antibody, an antibody fragment, a monoclonal antibody, an enzyme, an engineered protein, an immunogenic protein, a protein fragment, an immunoglobulin and any combination thereof.

According to embodiments of the present disclosure, a therapeutic protein treated by/resulting from the process of the present disclosure can be formulated into a pharmaceutical composition without any further purification and/or decontamination step.

According to embodiments of the present disclosure, the multi-column chromatography system used in the present process can be operated in a continuous mode and at steady state.

Various objects, features, aspects and advantages of the inventive subject matter will become more apparent from the following detailed description of preferred embodiments.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION OF THE INVENTION

Figure 1:
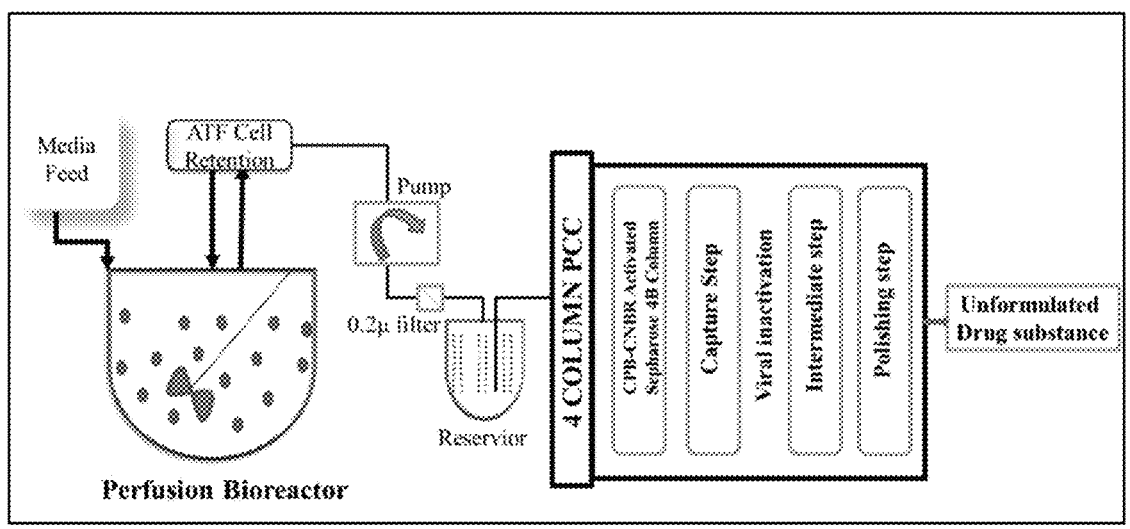
FIG. 1 illustrates an exemplary process flow for continuous processing of therapeutic protein on four columns, in accordance with embodiments of the present disclosure.

The following is a detailed description of embodiments of the present disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, process conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

Various terms are used herein. To the extent a term used in a claim is not defined below, it should be given the broadest definition persons in the pertinent art have given that term as reflected in printed publications and issued patents at the time of filing.

The term "continuous process" as used herein refers to any process having two or more processing steps in a series, wherein the output from an upstream step (unit operation) is transferred to a downstream step (unit operation) continuously till the final chromatography step and wherein it is not necessary for the upstream processing step to run to completion before the next processing step is started. In a continuous process some portion of the target product is always moving through the processing system. Ideally, a continuous process is regulated so that, to the greatest extent possible, every step or unit operation of the continuous process is running at the same time and at substantially the same production rate. In this way, compression of the cycle time is maximized and the shortest possible completion time is achieved.

The term "continuous transfer" refers to a product stream moving from an upstream unit operation to a downstream unit operation, means that the connections or links between the two unit operations are such that the upstream unit operation transfers a product stream (directly or through other components) to the second (downstream) unit operation, and that the downstream unit operation begins before the upstream unit operation runs to completion (that is, the two successive unit operations are processing the product streams flowing into them simultaneously for at least part of the overall process run of which the two unit operations comprise a part).

The term "perfusion cell culture process" as used herein refers to perfusion cultivation which is carried out by continuously feeding fresh medium to the bioreactor and constantly removing the cell-free spent medium while retaining the cells in the reactor; thus, a higher cell density can be obtained in perfusion cultures compared to continuous cultures, as cells are retained within the reactor via a cell retention device. The perfusion rate depends on the demand of cell line, the concentration of nutrients in the feed and the level of toxification The term "cell culture medium" refers to all kinds of media which are used in the context of culturing cells. Typically, a cell culture medium comprises amino acids, at least one carbohydrate as an energy source, trace elements, vitamins, salts and possibly additional components (e.g. in order to influence cell growth and/or productivity and/or product quality The term "therapeutic protein" means a recombinant protein that has been sufficiently purified or isolated from contaminating proteins, lipids, and nucleic acids present in a liquid culture medium or from a host cell (e.g., from a mammalian, yeast, or bacterial host cell) and biological contaminants (e.g., viral and bacterial contaminants), and can be formulated into a pharmaceutical product. Representative examples of therapeutic protein include, but are not limited to, an antibody, an antibody fragment, a monoclonal antibody, an enzyme, an engineered protein, an immunogenic protein, protein fragment, and an immunoglobulin.

The term "antibody" refers to functional component of serum and is often referred to either as a collection of molecules (antibodies or immunoglobulins, fragments, etc) or as a molecule. An antibody molecule is capable of binding to or reacting with a specific antigenic determinant, which in turn may lead to specific immunological effect or mechanisms.

The term "monoclonal antibody" refers to an antibody produced by a single clone of cells or cell line and consisting of identical antibody molecules.

The term "isoform" refers to any of two or more functionally similar proteins that have a similar but not identical amino acid sequence and are either encoded by different genes or by RNA transcripts from the same gene which have had different exons removed.

The term "heterogeneity" refers to a phenomenon wherein secreted antibodies have various discrete biochemical forms, such as, but not limited to, an extra amino acid or acids on the carboxy terminus of one or both of the antibody heavy chains.

The term "reducing the heterogeneity" as used herein refers to process for conversion of heterogeneous forms of monoclonal antibody to substantially pure, homogenous form.

The term "retention time" as used herein refers to the time in which halve of the quantity of a solute is eluted from the chromatographic system. It is determined by the length of the column and the migration velocity of the solute; which can be in the range of 1-30 minutes.

The term "multicolumn chromatography system" or "MCCS" means a system of a total of two or more interconnected or switching chromatography columns and/or chromatographic membranes. A non-limiting example of a multi-column chromatography system includes a periodic counter current chromatography system (PCC) containing a total of two or more interconnected or switching chromatography columns and/or chromatographic membranes.

The term "eluate/filtrate" is a term of art and means a fluid that is emitted from a chromatography column or chromatographic membrane that contains a detectable amount of a recombinant therapeutic protein.

Embodiments of the present disclosure relate to a bio-manufacturing process that enables continuous production of a therapeutic protein with reduced heterogeneity. The bio-manufacturing process disclosed herein utilizes a multi column chromatography system that performs the unit operations of reducing heterogeneity in a therapeutic protein, capturing the therapeutic protein and inactivating viruses, purifying the therapeutic protein, and polishing the purified therapeutic protein.

In an aspect, the present disclosure provides a continuous process for reducing heterogeneity of a therapeutic protein, the process including reducing one or more basic isoforms of the therapeutic protein in a single multi-column chromatography system.

In an embodiment, the multi-column chromatography system can include at least two chromatography columns.

In an embodiment, the multi-column chromatography system can include a column comprising carboxypeptidase B immobilized on sepharose.

In another aspect, the present disclosure provides a continuous process for reducing heterogeneity of a therapeutic protein, the process can include the steps of:
(a) providing a multi-column chromatography system comprising a first column, a second column, a third column and a fourth column;
(b) feeding a cell culture harvest comprising a therapeutic protein into the first column, thereby reducing heterogeneity of the therapeutic protein; wherein the first column comprising carboxypeptidase B immobilized on sepharose,
(c) feeding a flow-through from the first column into the second column, thereby capturing the therapeutic protein in the flow-through of the first column;
(d) feeding an eluate comprising the therapeutic protein from the second column into the third column to purify the therapeutic protein; and
(e) feeding a flow-through comprising the therapeutic protein from the third column into the fourth column to polish the therapeutic protein.

In an embodiment, the first, second, third and fourth columns of the multi-column chromatography system can be connected in sequential order in series or in parallel.

In an embodiment, the first column reduces heterogeneity of a therapeutic protein by reducing a proportion of basic isoforms of the therapeutic protein.

In an embodiment, the second column can be an affinity chromatography column.

In an embodiment, each of the third column and fourth column can be selected from the group consisting of anion exchange chromatography column, cation exchange chromatography column, hydrophobic interaction chromatography column, and multimodal chromatography column.

According to embodiments of the present disclosure, the multi-column chromatography system used in the present process can be operated in a continuous mode and at steady state.

In one preferred embodiment of the continuous process, a flow-through from the first column comprising a recombinant protein with reduced heterogeneity is either collected or continuously loaded on the second column. An eluate from the second column is collected such that the pH for the same is in the range of that required for the low pH viral inactivation, and holding the same in a reservoir for required incubation time. After viral inactivation, the pH of the eluate from the second column of the multi column chromatography system is adjusted to the pH and conductivity required for loading on third column by in-line buffer/solution addition. The eluate from second column is loaded on a pre-equilibrated third column for intermediate purification step for removal of other impurities, such as for example, HCP, HcDNA and virus. The third column can be operated in flow through or bind and elute mode. A flow-through from the third column is collected in a reservoir and then adjusted for pH and conductivity inline on system prior to loading on fourth column. It can also be directly loaded on fourth column if the sample conditions are same as that of the continuous process for the respective therapeutic proteins. The therapeutic protein can then be eluted from fourth column if operated in bind and elute mode or the flow-through can be collected if operated in flow through mode. So, entire continuous process for manufacturing therapeutic recombinant protein can be completed on single unit operation of multi column chromatography system. The therapeutic protein obtained from the process is pure, high volumetric productivity, streamlined process flow, low cycle time and reduced capital cost. An exemplary process flow for continuous processing of therapeutic protein on four columns is shown in FIG. 1.

In one embodiment, the first column of the multicolumn chromatography system performs the unit operation of reducing heterogeneity in a therapeutic protein by removing basic charge isoforms of the therapeutic protein.

In one embodiment, the process of heterogeneity removal can be performed using any chromatography system on which multiple columns can be connected comprising AKTA Avant 150, ÄKTA pcc 2 columns, ÄKTA pcc 3 columns, ÄKTA pcc 4 columns and BioSMB PALL.

In one embodiment, the intermediate purification and polishing steps can be performed in continuous manner using different chromatography methods such as anion exchange chromatography, cation exchange chromatography, hydrophobic interaction chromatography or multimodal chromatography. Suitable chromatography can be selected based on process parameters, desired quality, purity, recovery and productivity.

Examples of therapeutic proteins that can be prepared by/used in the process of the present disclosure can include, but not limited to, an antibody, an antibody fragment, a monoclonal antibody, an enzyme, an engineered protein, an immunogenic protein, a protein fragment, an immunoglobulin and any combination thereof.

In one embodiment, monoclonal antibody is selected from a naturally occurring antibody or a recombinant antibody selected from monoclonal antibody, modified antibody, derivative of antibody and fragment of antibody or any combination thereof.

In one embodiment, the therapeutic protein can be selected from, but not limited to, panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, blinatumomab, canakinumab, certolizumab, cetuximab, cixutumumab, daclizumab, denosumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, nivolumab, obinutuzumab, oregovomab, palivizumab, panitumumab, pertuzumab, ramucirumab, ranibizumab, rituximab, Secukinumab, tocilizumab, tositumomab, tralokinumab, tucotuzumab, trastuzumab, Ustekinumab, vedolizumab, veltuzumab, zalutumumab, zatuximab, enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine), alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, insulin or insulin analogs, mecasermin, factor VIII, factor VIIa, anti-thrombin III, protein C, human albumin, erythropoietin, granulocute colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha, acid β-galactosidase, β-galactosidase, neuraminidase, hexosaminidase A, and hexosaminidase B.

In preferred embodiments, a culture medium of therapeutic protein can be derived from any source. For example, but not limited to, from a recombinant cell culture (e.g., a recombinant bacterial, yeast, or mammalian cell culture). The culture medium can be obtained from a fed-batch cell culture, a fed-batch bioreactor containing a culture of cells that secrete the recombinant therapeutic protein or a perfusion cell culture. The liquid culture medium can also be a clarified liquid culture medium from a culture of bacterial or yeast cells that secrete the recombinant therapeutic protein.

In one embodiment of the present disclosure, C-terminal lysine residues on heavy chain of monoclonal antibodies can be truncated in a continuous process by passing a harvest recovered from perfusion cell culture on a column which has carboxypeptidase B enzyme immobilized on sepharose. The homogenous harvest produced from the said reaction is further transferred in a continuous manner to affinity chromatography column for further purification of monoclonal antibody.

In one embodiment of the present disclosure, the continuous process disclosed herein can reduce the amount of enzyme needed for reduction of C-terminal residues of monoclonal antibodies.

In one embodiment of the present disclosure, a harvested cell culture fluid continuously coming from a bioreactor through alternative tangential filtration can be loaded on to carboxypeptidase B immobilized column at a pH and then it can be continuously loaded on affinity columns connected in tandem in continuous chromatography system or in series or parallel on MCCS.

In certain preferred embodiments, protein concentration in cells cultured is in a concentration range of 50-2500 mg/L of harvested cell culture fluid.

In an embodiment, the basic isoforms of monoclonal antibody can be reduced in the range of 50-100 percent.

According to embodiments of the present disclosure, a therapeutic protein treated by/resulting from the process of the present disclosure can be formulated into a pharmaceutical composition without any further purification and/or decontamination step.

According to embodiments of the present disclosure, the process disclosed herein forms a continuous biological manufacturing system for therapeutic protein.

The present disclosure also provides process of preparation of resin for carboxypeptidase-coupled sepharose column and stability of resin used for processing of therapeutic protein.

EXAMPLES

The disclosure is further illustrated by the following examples which in no way should be construed as being further limiting. One skilled in art will readily appreciate that the specific methods and results described are merely illustrative.

Example 1: Preparation of Resin for the Process

The resin was prepared by following process:
1) CNBR-activated Sepharose™ 4B lyophilized powder was swelled in water and washed with 1 mM HCl. The resin was further washed with 0.1M sodium bicarbonate buffer, pH 10.0.
2) The buffer exchanged enzyme carboxypeptidase B was incubated with the resin at a ratio of 2:1 (CPB: Resin) at pH 10.0, overnight at 2-8° C. with gentle stirring.
3) The reaction mixture was brought to ambient temperature and sodium borohydride was added at a ratio of 4 mg/mL of coupled resin. The suspension was incubated for one hour at the ambient temperature.
4) The resin was loaded on a column and was washed extensively with 50 mM sodium phosphate buffer, pH 7.0.
5) The column was further washed with 20 mM Tris HCl, 150 mM NaCl, pH 9.0 before use.

Stability and Storage of in House CPB-CNBR-Activated Sepharose™ 4B Resin:

This resin was found stable for more than one year with many numbers of cycles, still viable when stored at 2-8 deg C. This resin can be used for continuous processing at room temperature for continuous processing without decrease in performance.

Example 2: Process for Reducing Antibody Variants

Two columns were connected continuous in one purification system where the inlet of CPB-Sepharose column is connected to the system and the outlet of the same column is used as the inlet of protein A column. The flow through coming out from the CPB-Sepharose column was directly loaded on to protein A column for capture step. The protein was finally eluted using elution buffer (FIG. 2).

1. The CPB-Sepharose column was connected in tandem with affinity column and the the clarified cell culture harvest from perfusion cell culture was loaded on the preequilibrated column at pH 7.0, wherein it can be equilibrated at pH 6.5-9.0 for more than approximately 25 min contact time on column 1
2. The flow through coming out from the CPB-Sepharose column was directly loaded on affinity column connected with the outlet of CPB-sepharose resin for capture of therapeutic protein.
3. The antibody captured on second column which was affinity column, was finally eluted with 0.1 M acetic acid, pH 3.0 and neutralized with 2 M Tris base. One control run was performed with the same harvest coming out from the perfusion bioreactor and directly loaded on protein A for capture step. Both protein A elution samples were analyzed by WCEX-HPLC for analysis of charge variants.

Figure 2:
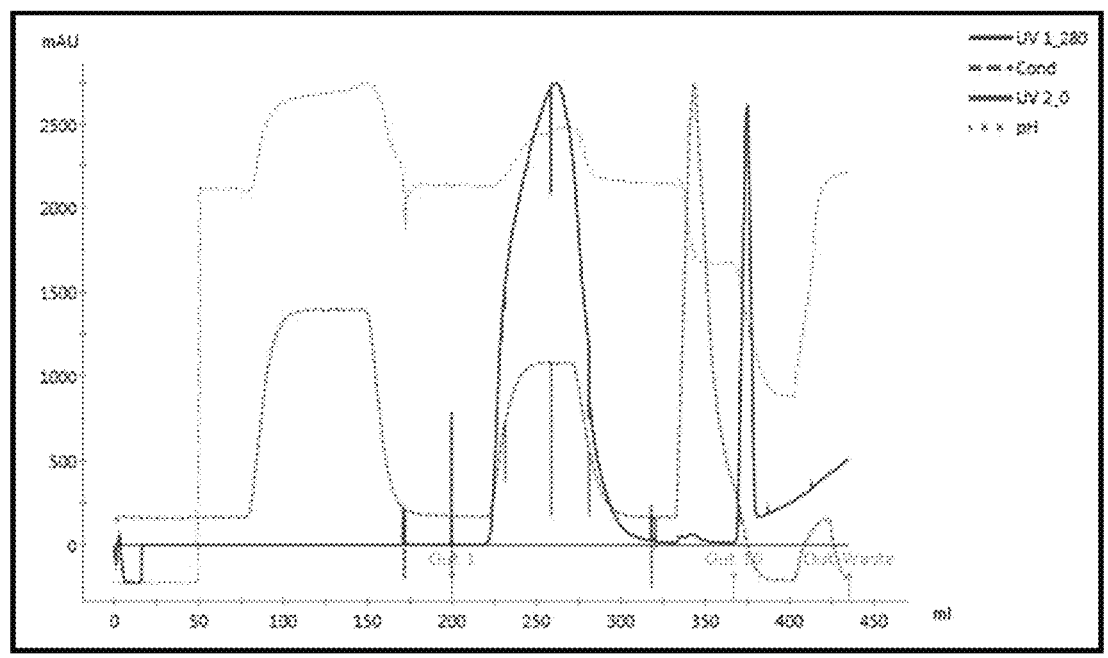
FIG. 2 shows chromatogram for two columns connected continuously in one purification system.

FIG. 2 shows chromatogram for two columns connected continuously in one purification system.

Figure 3:
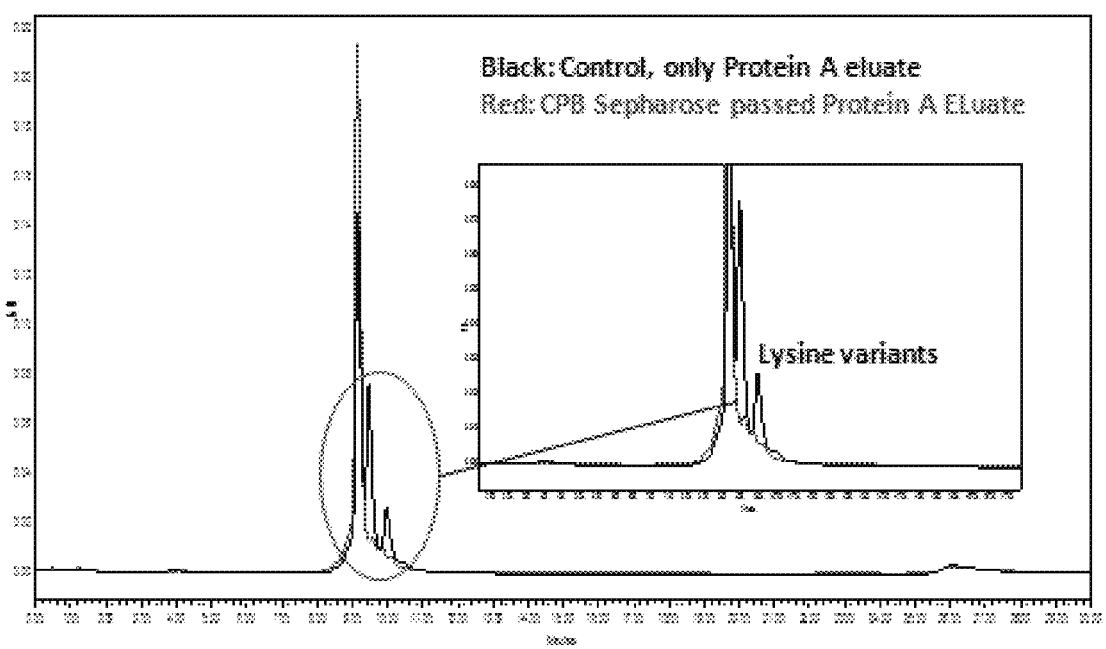
FIG. 3 shows chromatogram profile of CPB-CNBR-activated Sepharose™ 4B column followed by Protein A column run for mAb A in continuous mode at approx. 25 min RT.

FIG. 3 shows Chromatogram Profile of CPB-CNBR-activated Sepharose™ 4B column followed by Protein A column run for mAb A in continuous mode at approx. 25 min RT.

Example 3: Continuous Processing of Therapeutic Protein (mAb A)

Residence Time Study 1:

As the earlier chromatography run was performed with contact time on approximately 25 min on column 1, few more runs were performed to evaluate minimum contact time to be given to get optimum reduction in heterogeneity of therapeutic protein.

Figure 4:
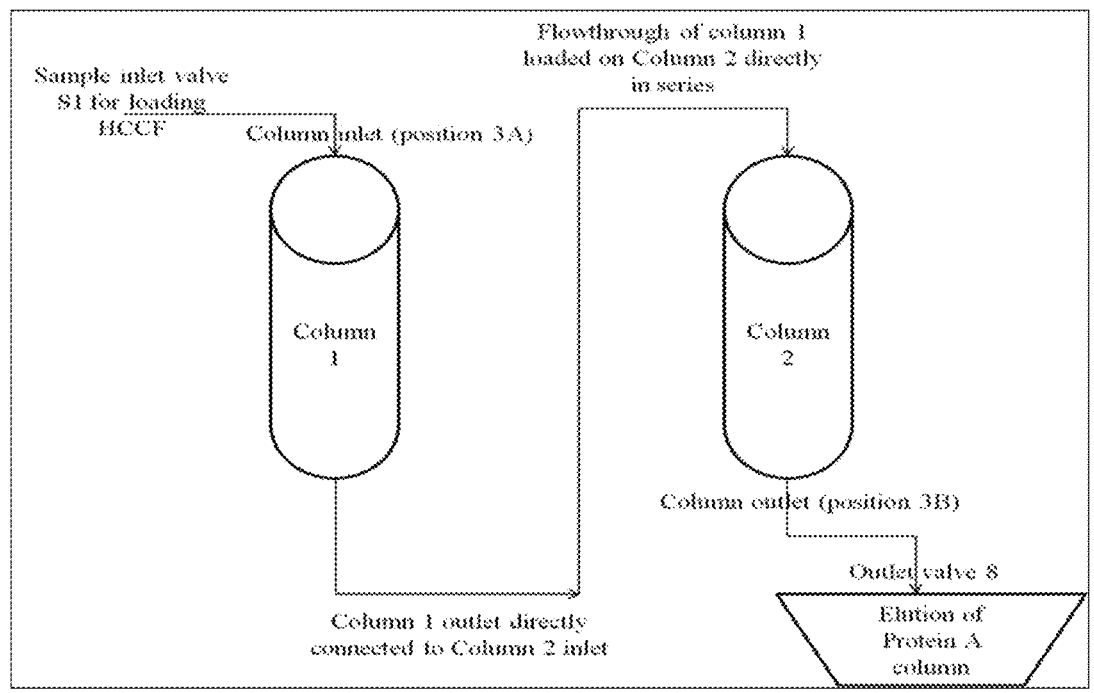
FIG. 4 shows continuous processing setup of Column 1 and Column 2 when operating at same flow rates.

The chromatographic run was performed using in house CPB-CNBR-activated Sepharose™ 4B column (Column 1, CV=10 ml) followed by Protein A (Mab Select SuRe™ pcc) column (column 2, CV=1 ml) (CPB-PA in series) in continuous mode (FIG. 4). The process was carried out on AKTA Avant 150 Process Chromatography System, GE Healthcare, with Therapeutic protein (mAb A) clarified cell culture fluid (approx. 40 mg) at flowrate of 0.5 ml/min maintaining residence time of 20 min on Column 1 and 2 min on Column 2 respectively. AKTA Avant system can be replaced with AKTA PCC system.

FIG. 4 shows continuous processing setup of Column 1 and Column 2 when operating at same flow rates.

Figure 5:
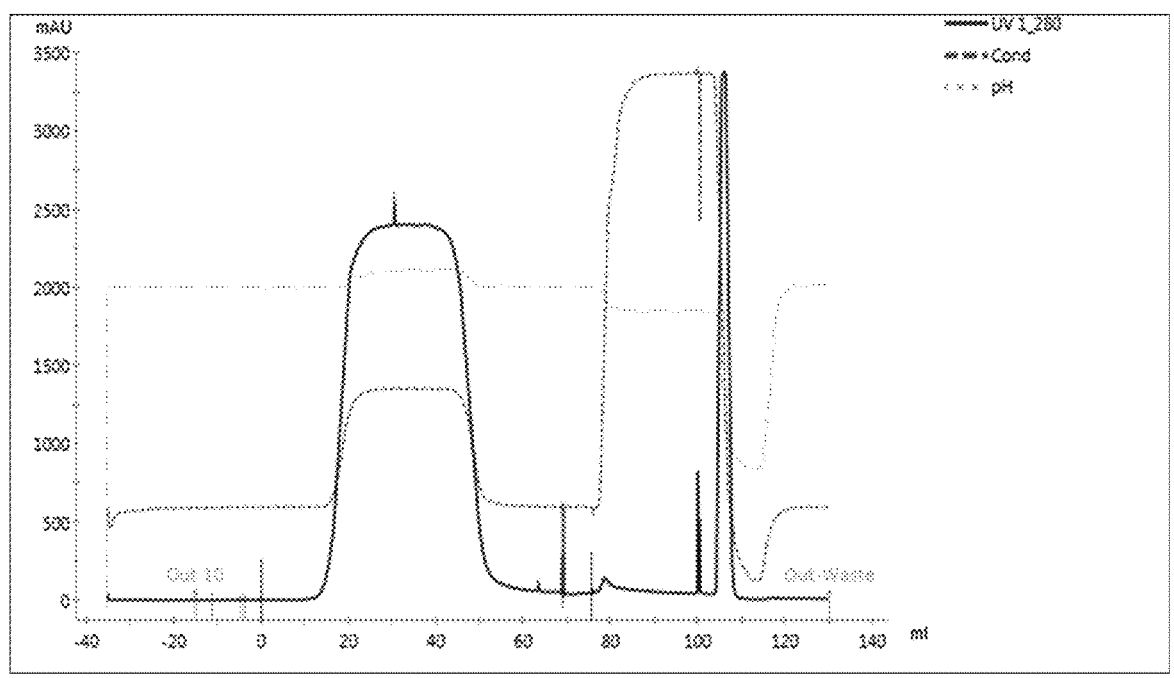
FIG. 5 shows chromatogram profile of CPB-CNBR-activated Sepharose™ 4B column followed by Protein A column run for mAb A in continuous mode at 20 min RT.

The neutralized sample (CPB-PA Elute) was submitted for WCEX analysis along with the control (only Protein A elute without CPB) (FIG. 5).

FIG. 5 shows chromatogram profile of CPB-CNBR-activated Sepharose™ 4B column followed by Protein A column run for mAb A in continuous mode at 20 min RT.

Figure 6:
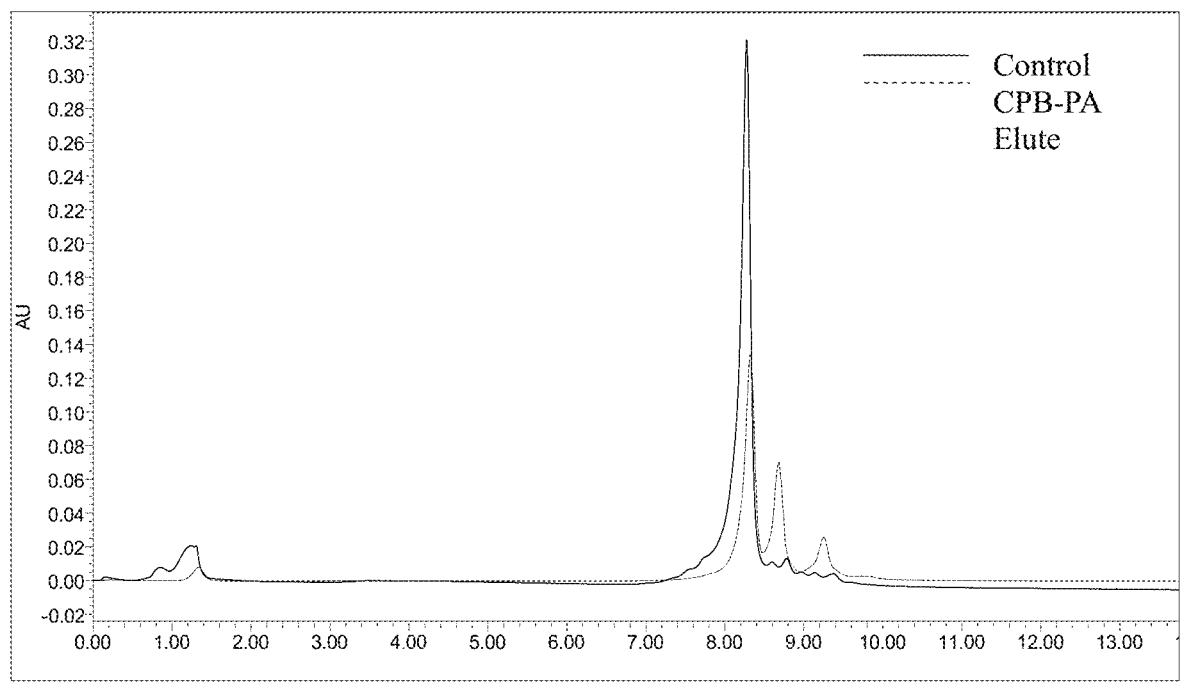
FIG. 6 depicts WCEX Analysis data overlay for Control and CPB-PA Elute.

The CPB-PA elute shown digestion/removal of basic variants in mAb A as compared to the control as shown in the WCEX analysis comparative data (FIG. 6).

FIG. 6 shows WCEX Analysis data overlay for Control and CPB-PA Elute. This experiment concluded that the CPB on column shown the activity or cleavage/digestion of basic variant at 20 min RT.

Residence Time Study 2:

To evaluate the minimum residence time (RT) on column, the flowrate was changed from 0.5 ml/min to 10 ml/min on CPB-CNBR-activated Sepharose™ 4B column (Column 1), maintaining RT of 2 min, whereas the flowrate on Protein A column (column 2) was 0.5 ml/min maintaining RT of 2 min. In this case, the flow-through of column 1 was collected and then reloaded on column 2 in continuous mode in order to maintain different RT and flow rate as column volumes are different. (FIG. 7).

Figure 7:
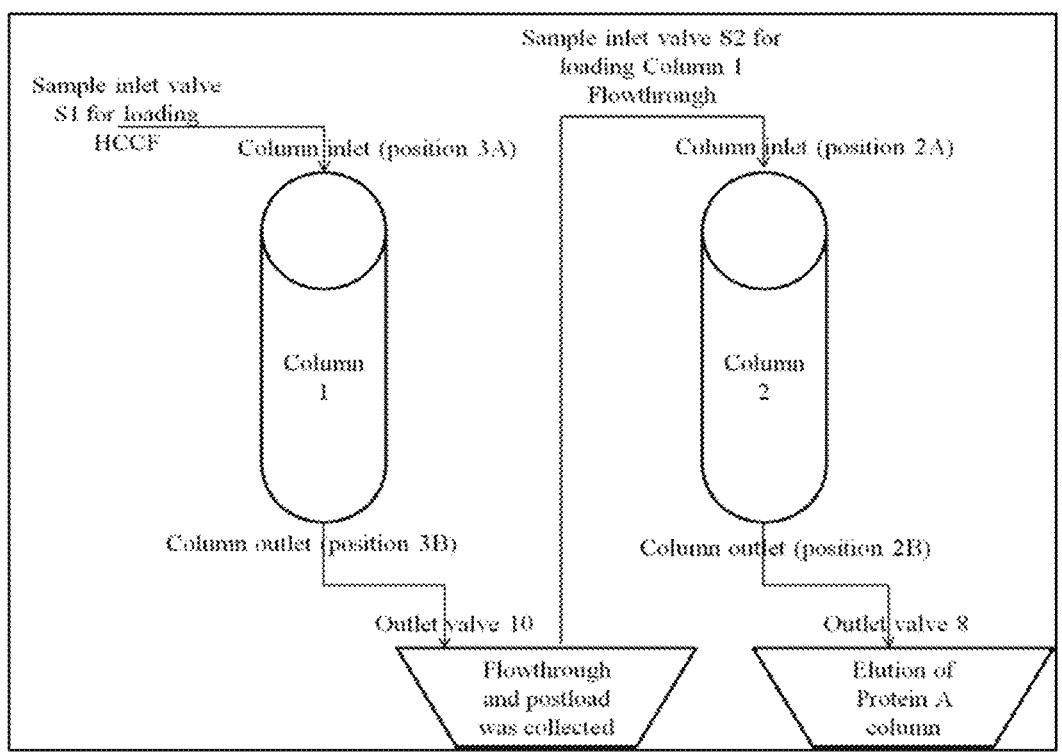
FIG. 7 shows continuous processing setup of Column 1 and Column 2 when operating at different flow rates.

FIG. 7 shows continuous processing setup of Column 1 and Column 2 when operating at different flow rates. The neutralized sample (CPB-PA Elute at 2 min RT) was submitted for WCEX analysis along with the control (only Protein A elute without CPB) and with that of CPB-PA Elute at 20 min RT. (FIG. 8).

Figure 8:
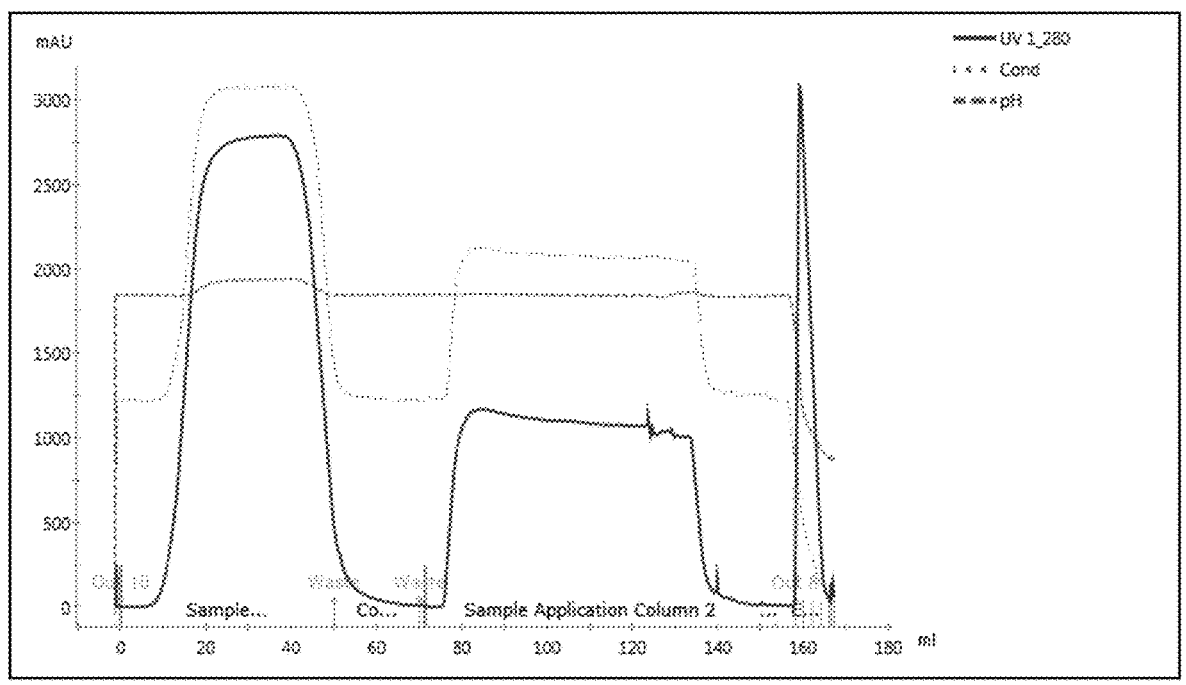
FIG. 8 shows chromatogram profile of CPB-CNBR-activated Sepharose™ 4B column followed by Protein A column run for mAb A in continuous mode at 2 min Rt.

FIG. 8 shows Chromatogram Profile of CPB-CNBR-activated Sepharose™ 4B column followed by Protein A column run for mAb A in continuous mode at 2 min Rt.

Figure 9:
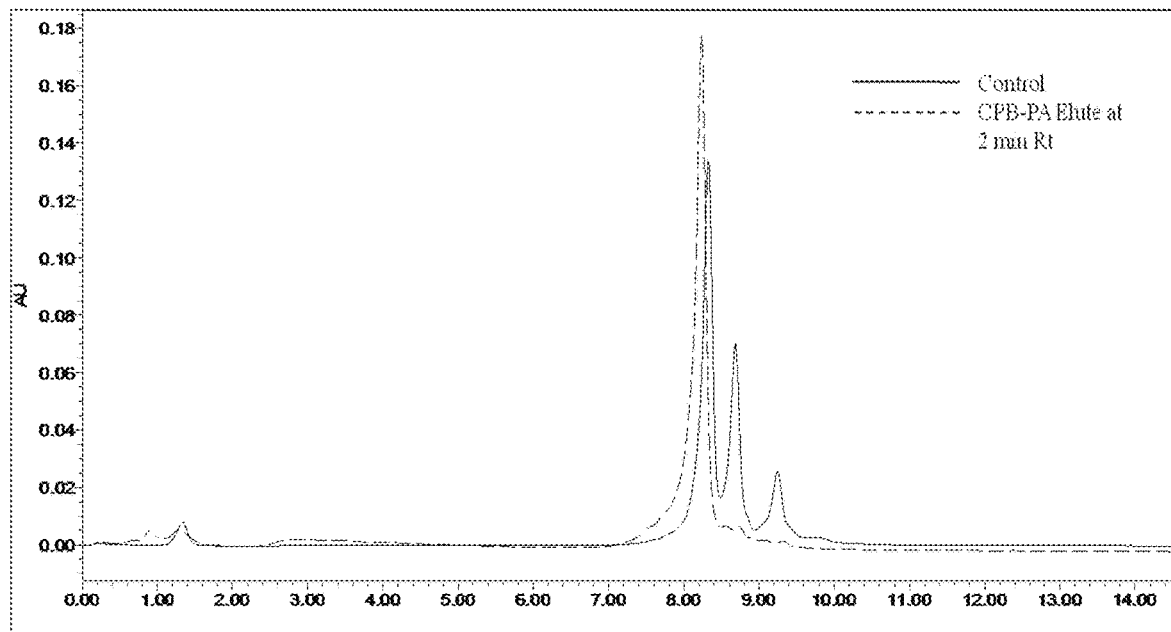
FIG. 9 depicts WCEX Analysis data overlay for Control and CPB-PA Elute at 2 min RT.

The CPB-PA elute shown digestion/removal of basic variants in mAb A as compared to the control at 2 min RT as well on Column 1 as shown in the WCEX analysis comparative data (FIG. 9).

FIG. 9 shows WCEX Analysis data overlay for Control and CPB-PA Elute at 2 min RT.

Comparison of Reduction at Two Different RT

Figure 10:
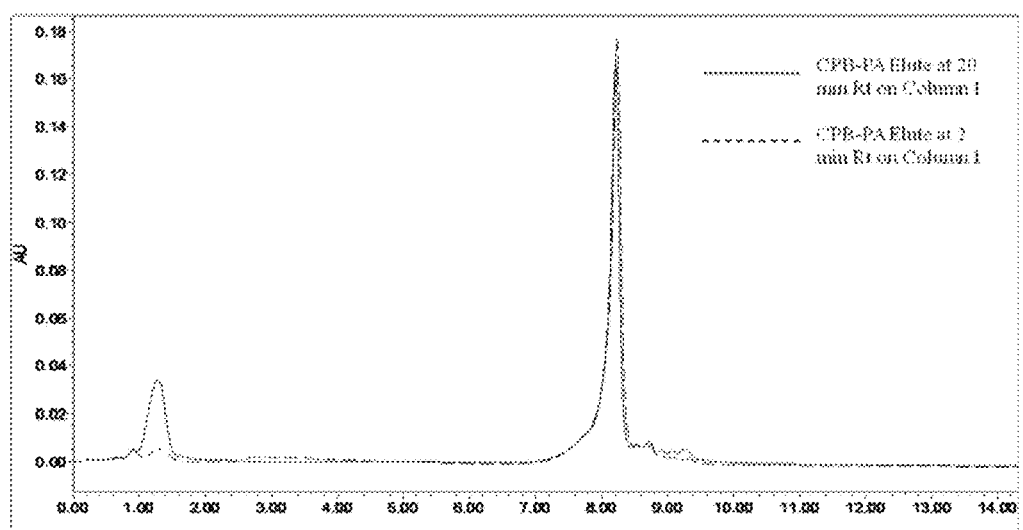
FIG. 10 shows WCEX Analysis data overlay for CPB-PA Elute at 20 min RT and 2 min RT respectively on Column 1 for mAb A.

At 2 min residence time on column 1, the digestion was significantly comparable with that of at 20 min RT on column 1 (FIG. 10). FIG. 10 shows WCEX Analysis data overlay CPB-PA Elute at 20 min RT and 2 min RT respectively on Column 1 for mAb A. Hence, the chromatography runs can be successively operated at 2 min residence time as well. The residence time lower than 2 min can also be evaluated.

Example 4: Process for Reducing Basic Isoforms on mAb B

As carboxypeptidase B preferentially acts upon the basic amino acids, such as arginine and lysine. Therefore, the resin can be used for removal of charged isoforms belonging to any class of IgGs or monoclonal antibodies. The removal of such charged isoforms in first step itself in continuous mode can yield a product with high quality, purity with high recovery. Another mAb model evaluated for the removal of charged isoforms/basic variants using the CPB-CNBR-activated Sepharose™ 4B column followed by Protein A column in continuous mode at 2 min RT was mAb B (FIG. 11).

Figure 11:
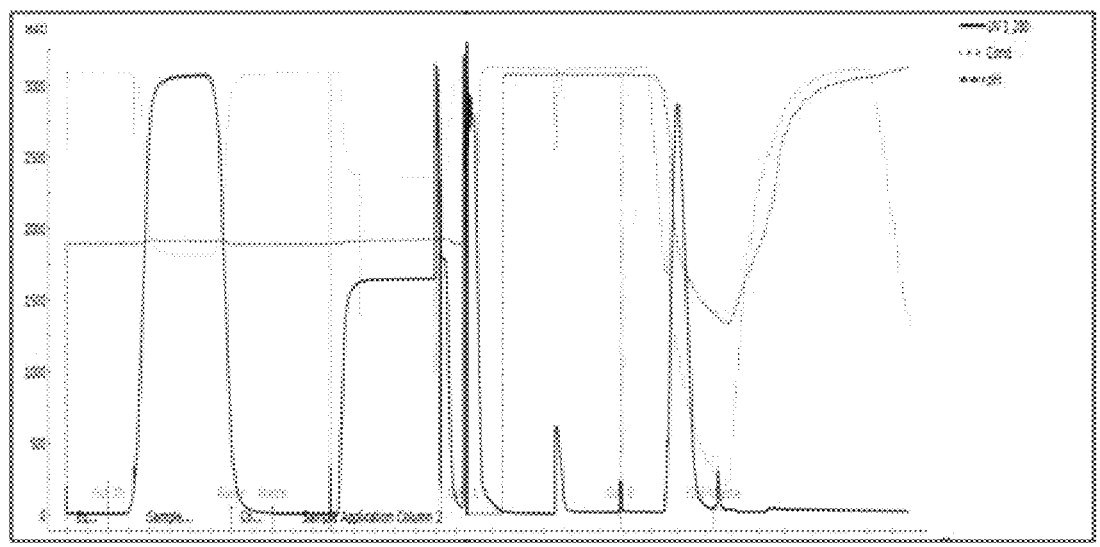
FIG. 11 shows chromatogram profile of CPB-CNBR-activated Sepharose™ 4B column followed by Protein A column run for mAb B in continuous mode at 2 min RT.

FIG. 11 shows Chromatogram Profile of CPB-CNBR-activated Sepharose™ 4B column followed by Protein A column run for mAb B in continuous mode at 2 min RT.

Figure 12:
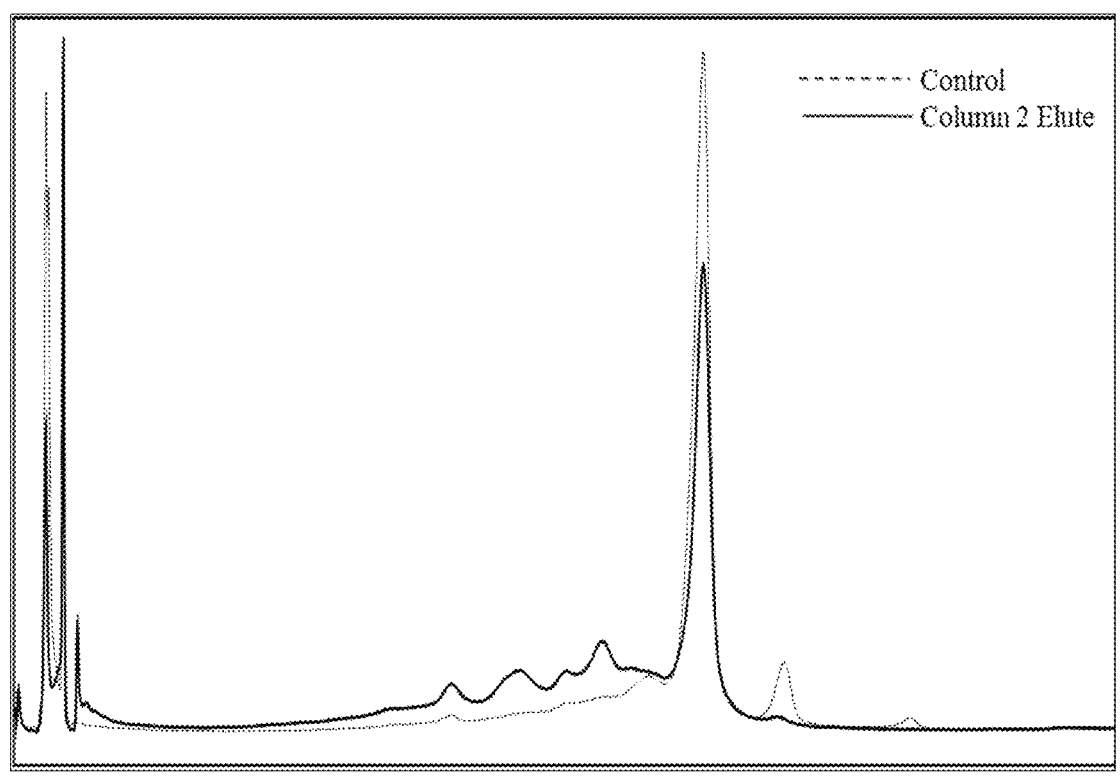
FIG. 12 shows WCEX Analysis data overlay for mAb B control and mAb B CPB-PA Elute at 2 min RT.

The CPB-PA elute shown digestion/removal of basic variants in mAb B as compared to the control (neutralized Protein A elute only without CPB-CNBR-activated Sepharose™ 4B column) as shown in the WCEX analysis comparative data (FIG. 12). Hence, it can be concluded that this strategy is applicable for any monoclonal antibodies belonging to all class of IgGs for removal of basic charge variants.

Example 5: Process for Reducing Basic Isoforms on mAb a at Different Loading Density on Three Columns To evaluate the maximum loading capacity on CPB-CNBR-activated Sepharose™ 4B column, different loading densities were evaluated in continuous mode using mAb A clarified cell culture fluid as mentioned in Table No. 1. The chromatographic runs were performed using in house CPB-CNBR-activated Sepharose™ 4B column (Column 1) followed by Protein A (Mab Select SuRe LX) column (column 2) (CPB-PA in series) in continuous mode. The process was carried out on ÄKTA pcc (three column Periodic Counter current chromatography, 3C PCC), GE Healthcare, with mAb A clarified cell culture fluid from perfusion culture at flowrate of 5 ml/min when one CPB-CNBR-activated Sepharose™ 4B column (Column 1) and two Protein A columns (Column 2) are connected parallely. The residence time maintained on Column 1 is equivalent to 1.7 min which was less than earlier studies and on column 2 was approximately 4.4 min (as resin used is MabSelect SuRe LX).

TABLE NO. 1

The loading details on Column 1 and Column 2

| Sr. No. | Volume of load (ml) | Total Protein (mg) | Column Volume of Column 1 (ml) | Loading density on Column 1 (mg/ml) | Column Volume of Column 2 (ml) | Loading density on Column 2 (mg/ml) | Time for loading (min) |
|---|---|---|---|---|---|---|---|
| 1* | 30 | 40 | 10 | 4 | 1 | 40.0 | 80 |
| 2^π | 60 | 85 | NA | NA | 22 | 4 | 12 |
| 3 | 60 | 85 | 8.5 | 10 | 22 | 4 | 12 |
| 4 | 120 | 170 | 8.5 | 20 | 22 | 8 | 24 |
| 5 | 240 | 341 | 8.5 | 40 | 22 | 15 | 48 |
| 6 | 480 | 682 | 8.5 | 80 | 22 | 31 | 96 |

Figure 13:
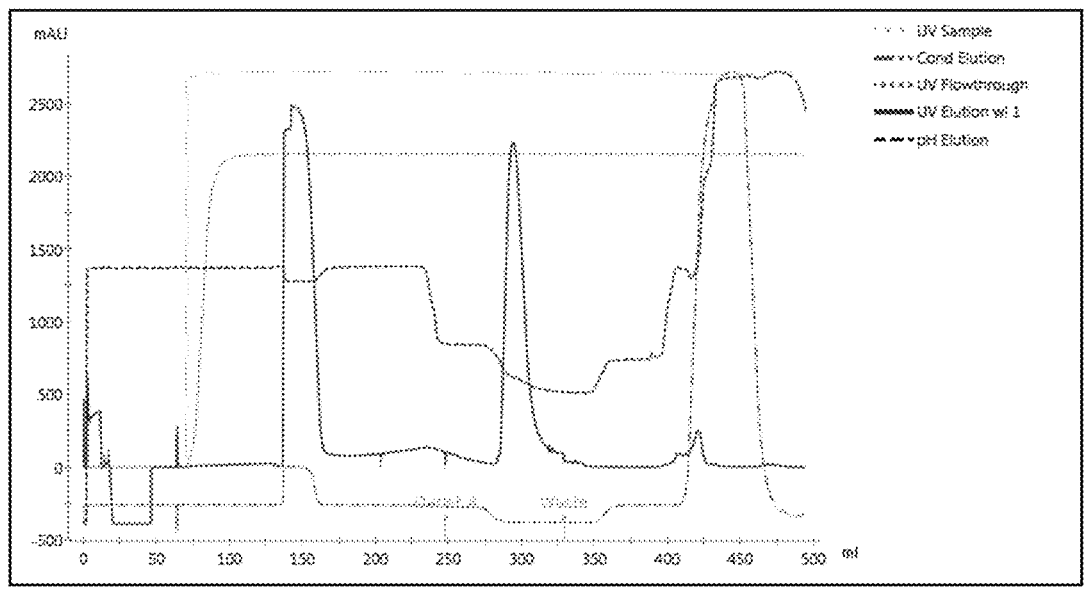
FIG. 13 shows chromatogram profile of Protein A column run for mAb A as control on ÄKTA pcc (3C pcc).
Figure 14:
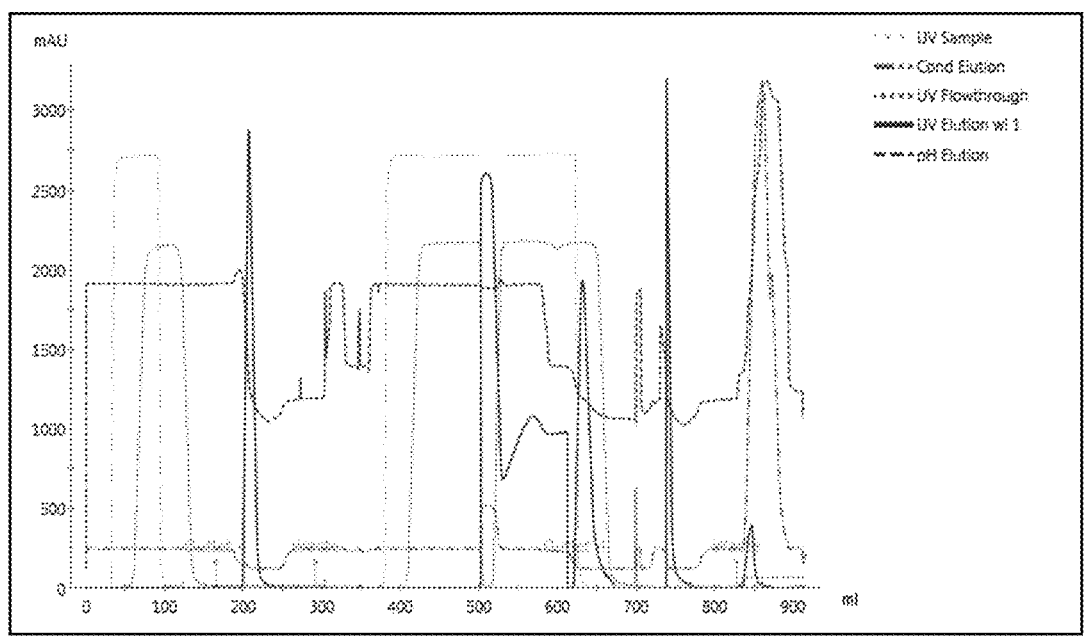
FIG. 14 shows chromatogram profile for loading density of 10 mg/ml, 20 mg/ml and 40 mg/ml respectively, on CPB-CNBR-activated Sepharose™ 4B column (Column 1) followed by Protein A column run for mAb A in continuous mode on ÄKTA pcc (3C pcc).

*The chromatographic run as per the conditions mentioned in Sr. No. 1 was performed earlier (FIG. 5)
^πControl Run A control run was performed using only protein A column for WCEX analysis comparison as mentioned in Table 1. The chromatography run as per conditions mentioned Sr. No. 3, 4, 5 and 6 wherein the loading density on Column 1 were 10 mg/ml, 20 mg/ml, 40 mg/ml and 80 mg/ml respectively was carried out continuously. In this chromatography run, one CPB-CNBR-activated Sepharose™ 4B column (Column 1) and two Protein A columns (Column 2) were connected parallel and Column 1 and column 2 were run in series (FIG. 13 and FIG. 14 for chromatogram profile). The neutralized samples were given for WCEX analysis for comparison with control.

FIG. 13 shows Chromatogram Profile of Protein A column run for mAb A as control on ÄKTA pcc (3C pcc).

FIG. 14 shows Chromatogram Profile for loading density of 10 mg/ml, 20 mg/ml and 40 mg/ml respectively on CPB-CNBR-activated Sepharose™ 4B column (Column 1) followed by Protein A column run for mAb A in continuous mode on AKTA pcc (3C pcc).

Figure 15:
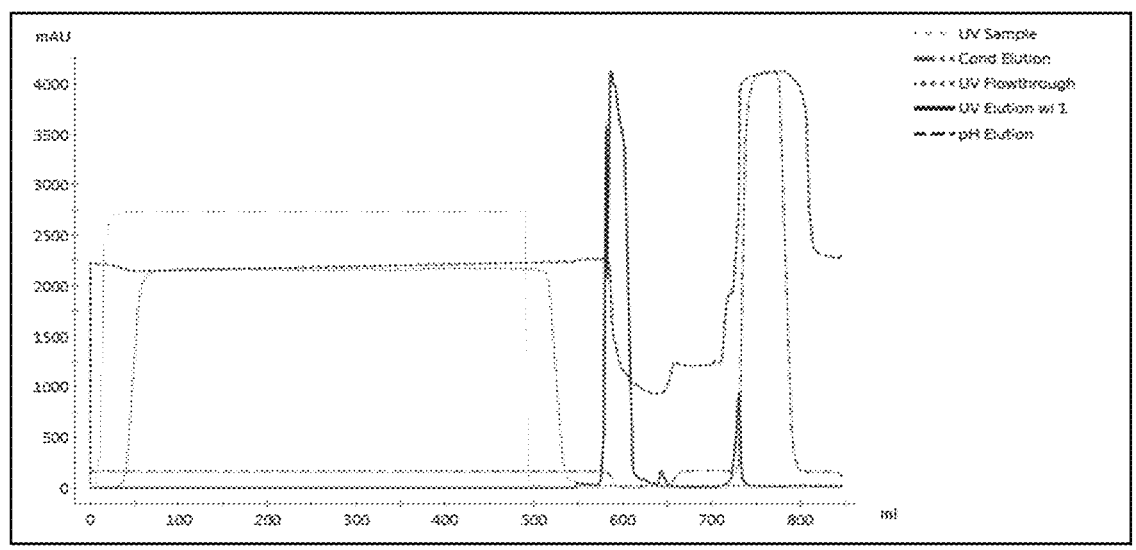
FIG. 15 shows chromatogram profile for loading density of 80 mg/ml on CPB-CNBR-activated Sepharose™ 4B column (Column 1) followed by Protein A column run for mAb A in continuous mode on ÄKTA pcc (3C pcc).

FIG. 15 shows Chromatogram Profile for loading density of 80 mg/ml on CPB-CNBR-activated Sepharose™ 4B column (Column 1) followed by Protein A column run for mAb A in continuous mode on AKTA pcc (3C pcc).

Figure 16:
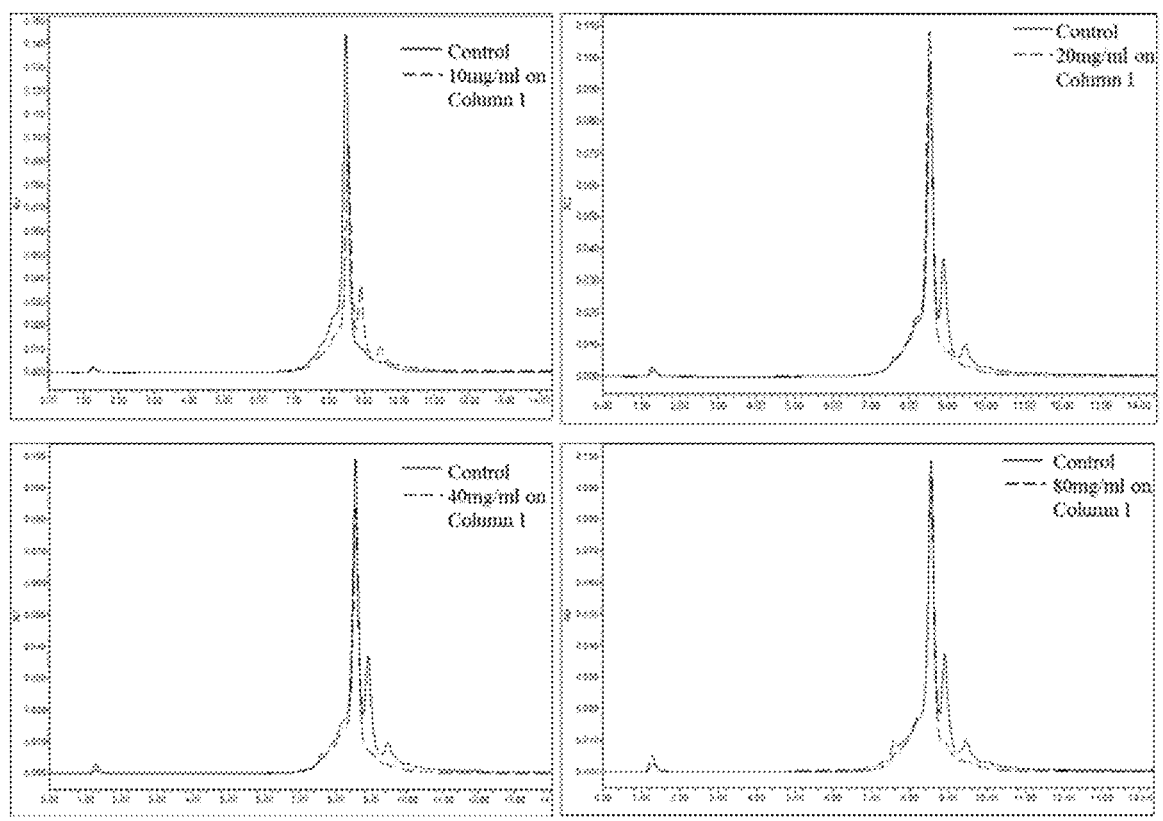
FIG. 16 depicts WCEX Analysis data overlays of neutralized CPB-PA Elute for individual loading density with the Control.

FIG. 16 shows WCEX Analysis data overlays of neutralized CPB-PA Elute for individual loading density with the Control. As observed in FIG. 16, the resin was showing activity or decrease in basic charges isoforms when compared to control. So, this resin may also work beyond 80 mg/ml of loading density on column 1, wherein, if column volume of Protein A resin also remains same as CPB-CNBR-activated Sepharose™ 4B column, then, 2 column of Protein A in parallel will be required to suffice the quantity of output from that of one column 1.

Figure 17:
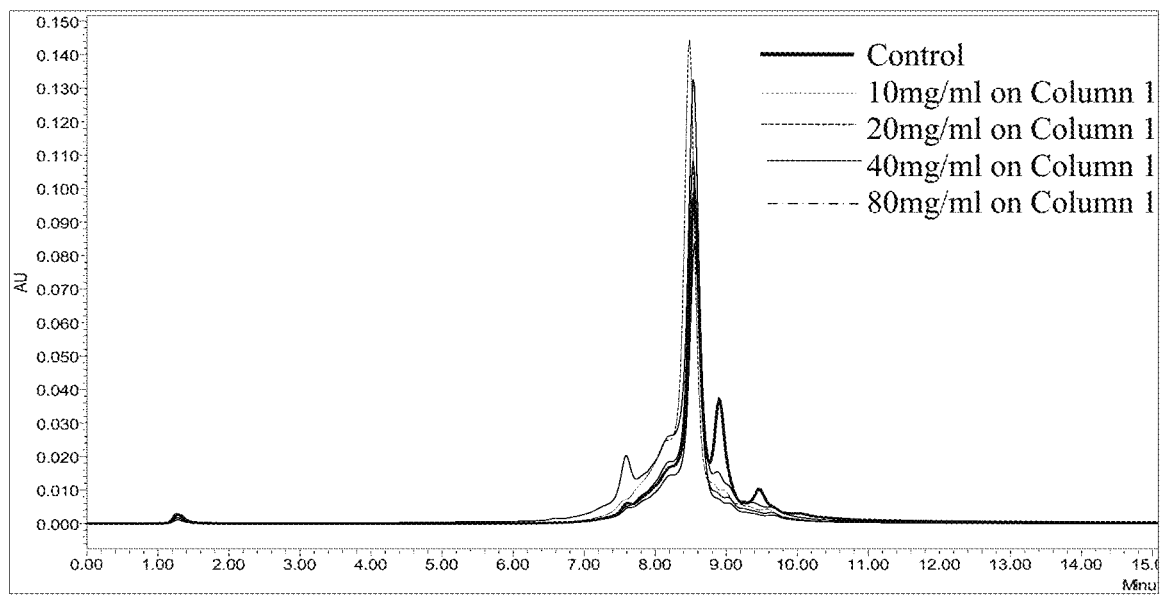
FIG. 17 depicts WCEX Analysis data overlays CPB-PA Elute along with control at different loading densities on Column 1 for mAb A.

FIG. 17 shows WCEX Analysis data overlays CPB-PA Elute along with control at different loading densities on Column 1 for mAb A. When WCEX analysis data overlays for all the different loading densities are compared, it was observed that, though there was decrease in basic charged isoforms in all samples, slight increase in the acidic variants was seen in case of 80 mg/ml of loading density on column 1 (FIG. 17). This can be due to higher loading density i.e. higher ratio of protein:CPB or due to higher loading time. But, as the residence time in all the runs were same, 1.7 min, and also one comparative data with condition 1 mentioned in Table 1. where the loading time was 80 min on column 1, there was no increase in acidic isoforms (FIG. 5). Therefore, the probable reason may be the total protein loaded on column 1 when moves forward (flow-through mode) on column 2, there may be a gradual increase in acidic variants with time and quantity of protein loaded, and gets accumulated on Column 2 (bind and elute mode), the total protein eluted contains the increase acidic forms. Hence, it will be better if the column 1 is regenerated with buffers of pH not less than pH 3.0 comprising 50 mM Sodium acetate, pH 5.0, or other similar buffers, between the runs where we get the required quality as well as quantity.

Figure 18:
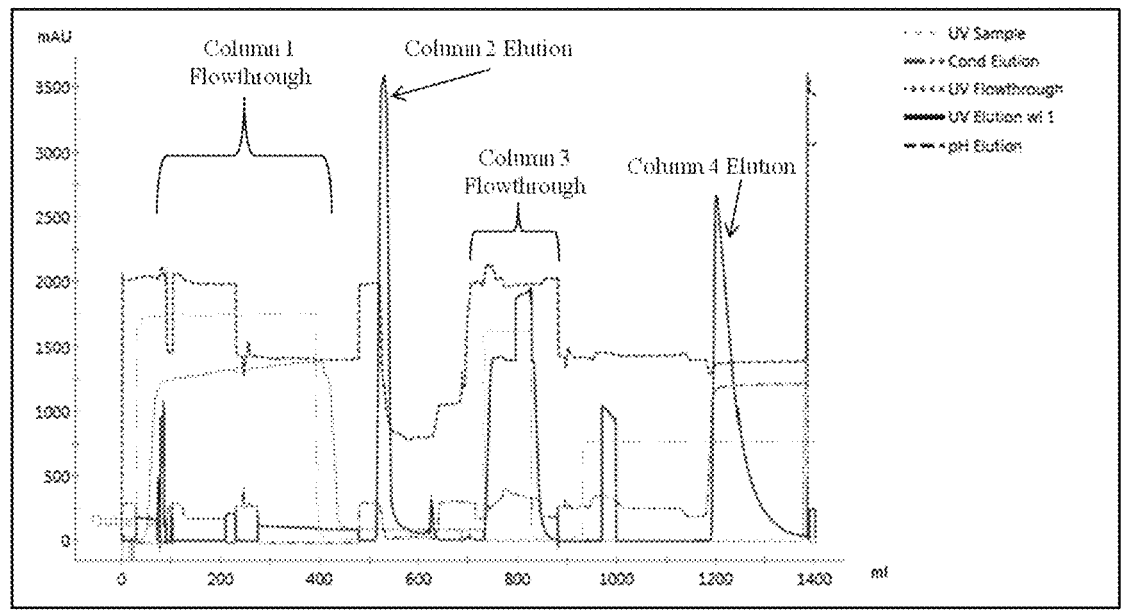
FIG. 18 shows chromatogram profile for continuous processing for mAb A on ÄKTA pcc (4C PCC).

Example 6: Continuous Process for Reducing Heterogeneity of Therapeutic Protein (mAb A) on 4 Columns in One-Unit Operation The chromatographic runs were performed using in continuous mode with 4 columns in parallel running in series on ÄKTA pcc (three column Periodic Counter current chromatography, 4C PCC), GE Healthcare, with mAb A clarified cell culture fluid from perfusion culture at flowrate of 5 ml/min. (FIG. 18). In house CPB-CNBR-activated Sepharose™ 4B column (Column 1) was followed by Protein A (Mab Select SuRe LX) column (column 2), followed Viral inactivation and Anion Exchange Chromatography (Q Sepharose Fast Flow) (Column 3) and that followed by Cation Exchange chromatography (SP Sepharose Fast Flow) (Column 4) in continuous mode. The process not limited to the above given scheme and other chromatography techniques and resin chemistry can also be incorporated like hydrophobic interaction chromatography or Mixed mode chromatography based on requirement of quality, purity and productivity or recovery. The sequence of chromatography step can also be changed based on requirement.

Column wise buffer used are illustrated below. The other combinations of buffers can also be used in same range of pH and conductivity for desired quality and productivity 1) Column 1: Column volume=8.5 ml, Loading density=60 mg/ml
   Equilibration and Post load wash: 50 mM Trsi HCl, pH 7.0±0.2, conductivity 4.0±1.0 mS/cm
   Regeneration: 50 mM Sodium acetate, pH 5.0±0.2, Conductivity 3.6±1.0 mS/cm
2) Column 2: Column volume=22 ml, Loading density=23 mg/ml
   Equilibration and Post load wash: 50 mM Trsi HCl, pH 7.0±0.2, conductivity 4.0±1.0 mS/cm
   Elution: 100 mM Acetic acid, pH 3.0±0.2
   Regeneration: 500 mM Sodium Hydroxide
3) Column 3: Column volume=20 ml, Loading density=25 mg/ml
   Equilibration and Post load wash: 50 mM Trsi HCl, pH 7.0±0.2, conductivity 4.0±1.0 mS/cm
   Regeneration: 500 mM Sodium Hydroxide 4) Column 4: Column volume=20 ml, Loading density=25 mg/ml
   Equilibration and Post load wash: 50 mM Sodium acetate, pH 5.0±0.2,
   Conductivity 3.6±1.0 mS/cm
   Elution: 50 mM Sodium acetate, 150 mM NaCl pH 5.0 Conductivity 15.0±1.0 mS/cm
   Regeneration: 500 mM Sodium Hydroxide In this continuous process, the Column 1 was loaded with the loading density of 60 mg/ml on 8.5 ml CV column and flow through was continuously passed on Column 2 for capture of mAb A. The bound protein was eluted with 100 mM acetic acid with CV volume such that the pH of elute is equivalent to the pH required for viral inactivation. Viral inactivation was carried out at pH≤3.6, holding for 1 hr and then neutralization of Protein A elute was done by inline addition of required volume of 2M Tris Base. The pH and conductivity of the neutralized protein A elute was equivalent to that required for loading on column 3 which claims HCP, HcDNA and virus removal thereof, pH 7.0±0.2 and conductivity was lesser than 10 mS/cm, and was found to be approximately 4.5±1.0 mS/cm. This neutralized protein A elute was passed on pre equilibrated column 3, operated in flow-through mode and the flow-through of the same was collected. As column 4 was to be operated in bind and elute mode at pH 5.0 and conductivity ≤6.0 mS/cm (but not bound to these conditions only), again in line addition of required quantity of acid, in this case 100 mM acetic acid was performed as load preparation step for column 4 loading. The pH of load was found to be 5.0±0.2 and conductivity was ≤3.5 mS/cm and was loaded on column 4, and the bound protein was eluted with 50 mM Sodium acetate, 150 mM NaCl pH 5.0 Conductivity 15.0±1.0 mS/cm and samples were submitted for WCEX analysis for comparison in removal of charge isoforms. The regeneration of all the columns and preparation for next run was done. The chromatogram profile and analytical data are shown in FIGS. 18 and 19 respectively.

FIG. 18 shows Chromatogram profile for Continuous Processing for mAb A on ÄKTA pcc (4C PCC). If removal of other product related impurities is required, then column 4 process condition can be modified for linear or step gradient or other mode of interactions. This process parameters can be modified depending on factors like nature of therapeutic protein, Isoelectric point, quality, purity and productivity, cost efficiency, ease of operation.

Figure 19:
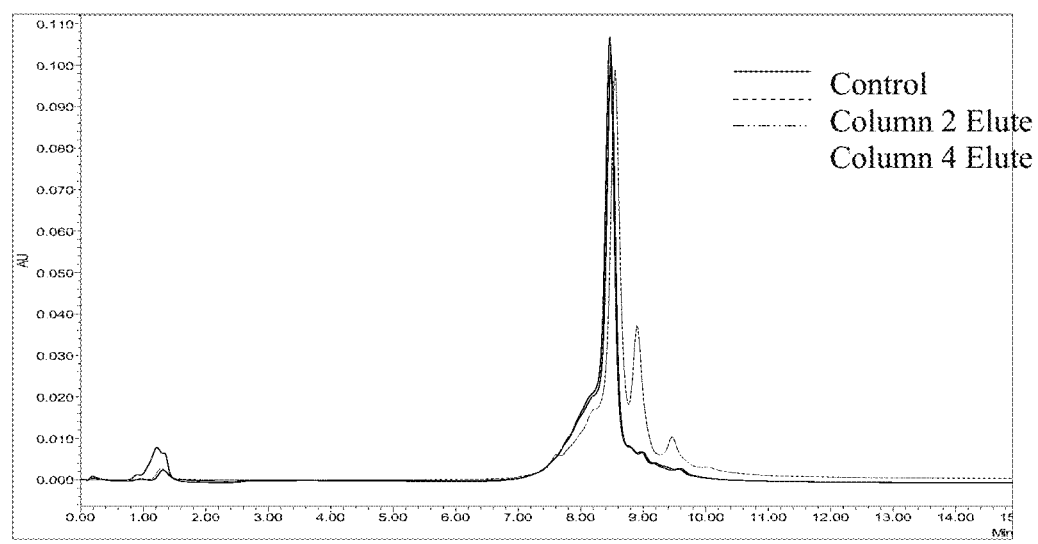
FIG. 19 depicts WCEX Analysis data overlays control with Column 2 Elute and Column 4 Elute from continuous processing.

Both the Column 2 elute (neutralized protein A elute sample) and Column 4 elute samples were given for WCEX analysis along with control sample belonging to loading density experiment (FIG. 19).

FIG. 19 shows WCEX Analysis data overlays control with Column 2 Elute and Column 4 Elute from continuous processing. The Column 2 and Column 4 shows same WCEX profile and shows removal of basic isoforms, wherein there is no increase in the acidic variants at this loading density (60 mg/ml) that was observed at loading density of 80 mg/ml. Therefore, the optimum operating conditions for this in house CPB-CNBR-activated Sepharose™ 4B column may comprise of loading density of ≤80 mg/ml, for loading time of approximately 1-2 h for mAb A, and RT of ≥1.7 min, but not limited to these conditions after which regeneration may be incorporated between the runs in order to get consistent results.

We claim:

1. A continuous process for reducing heterogeneity of a therapeutic protein, the process comprises reducing one or more basic isoforms of the therapeutic protein in a single multi-column chromatography system comprising a first, second, third and fourth columns connected in sequential order in series or in parallel, which includes a first column comprising carboxypeptidase B immobilized on Sepharose; and feeding a flow-through from the first column into the second column.

2. A continuous process for reducing heterogeneity of a therapeutic protein, the process comprising the steps of:
   (a) providing a multi-column chromatography system comprising a first column, a second column, a third column and a fourth column;
   (b) feeding a cell culture harvest comprising-a therapeutic protein into the first column, thereby reducing heterogeneity of the therapeutic protein; wherein the first column comprises carboxypeptidase B immobilized on Sepharose;
   (c) feeding a flow-through from the first column into the second column, thereby capturing the therapeutic protein in the flow-through of the first column;
   (d) feeding an eluate comprising the therapeutic protein from the second column into the third column to purify the therapeutic protein; and
   (e) feeding a flow-through comprising the therapeutic protein from the third column into the fourth column to polish the therapeutic protein.

3. The process as claimed in claim 2, further comprising collecting the eluate comprising the therapeutic protein from the second column, and holding the eluate comprising the therapeutic protein at a low pH for viral inactivation.

4. The process as claimed in claim 2, further comprising subjecting the eluate comprising the therapeutic protein from the second column to pH and conductivity adjustments prior to feeding into the third column.

5. The process as claimed in claim 2, further comprising subjecting the flow-through comprising the therapeutic protein from the third column to pH and conductivity adjustments prior to feeding into the fourth column.

6. The process as claimed in claim 2, wherein the first, second, third and fourth columns are connected in sequential order in series or in parallel.

7. The process as claimed in any of the preceding claims, wherein the first column reduces heterogeneity of the therapeutic protein by reducing a proportion of basic isoforms of the therapeutic protein.

8. The process as claimed in claim 2, wherein the second column is an affinity chromatography column.

9. The process as claimed in claim 2, wherein each of the third column and fourth column is selected from the group consisting of anion exchange chromatography column, cation exchange chromatography column, hydrophobic interaction chromatography column, and multimodal chromatography column.

10. The process as claimed in claim 2, wherein the therapeutic protein is selected from an antibody, an antibody fragment, a monoclonal antibody, an enzyme, an engineered protein, an immunogenic protein, a protein fragment, an immunoglobulin or any combination thereof.

11. The process as claimed in claim 2, wherein the therapeutic protein is selected from the group consisting of: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, blinatumomab, canakinumab, certolizumab, cetuximab, cixutumumab, daclizumab, denosumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, nivolumab, obinutuzumab, oregovomab, palivizumab, panitumumab, pertuzumab, ramucirumab, ranibizumab, rituximab, Secukinumab, tocilizumab, tositumomab, tralokinumab, tucotuzumab, trastuzumab, Ustekinumab, vedolizumab, veltuzumab, zalutumumab, zatuximab, enzymes, proteins, immunogenic or antigenic proteins or protein fragments, alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, insulin or insulin analogs, mecasermin, factor VIII, factor Vila, anti-thrombin III, protein C, human albumin, erythropoietin, granulocute colony stimulating factor, granulocyte macrophage colony stimulating factor, interleukin-11, laronidase, idursuphase, galsulphase, a-1-proteinase inhibitor, lactase, adenosine deaminase, tissue plasminogen activator, thyrotropin alpha, acid β-galactosidase, (β-galactosidase, neuraminidase, hexosaminidase A, and hexosaminidase B.

12. The process as claimed in claim 2, further comprising formulating the polished therapeutic protein into a pharmaceutical composition.

13. The process as claimed in claim 2, wherein the multi-column chromatography system is operated in a continuous mode.

\* \* \* \* \*